(12) United States Patent
Weekes

(10) Patent No.: US 9,936,960 B2
(45) Date of Patent: Apr. 10, 2018

(54) DETACHABLE ORTHOPAEDIC REAMER HANDLE

(71) Applicant: Symmetry Medical Manufacturing, Inc., Warsaw, IN (US)

(72) Inventor: Stuart Weekes, Oxford (GB)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 702 days.

(21) Appl. No.: 14/548,573

(22) Filed: Nov. 20, 2014

(65) Prior Publication Data

US 2016/0143649 A1 May 26, 2016

(51) Int. Cl.
*A61B 17/16* (2006.01)
*A61B 17/00* (2006.01)

(52) U.S. Cl.
CPC ...... *A61B 17/1622* (2013.01); *A61B 17/1624* (2013.01); *A61B 17/1666* (2013.01); *A61B 2017/0046* (2013.01); *A61B 2017/00477* (2013.01)

(58) Field of Classification Search
CPC  A61B 17/1666; B25B 23/0028; B25G 1/066; B25G 3/20; B25G 1/06; B25G 1/043; B25G 3/22; B25F 5/02; Y10T 16/4713; B23B 45/001
See application file for complete search history.

(56) References Cited

U.S. PATENT DOCUMENTS

| | | | |
|---|---|---|---|
| 7,993,348 B2* | 8/2011 | Conte | A61B 17/1617 606/79 |
| 9,078,672 B1* | 7/2015 | Rosse | A61B 17/1631 |
| 9,308,638 B2* | 4/2016 | Kondo | |
| 2014/0020210 A1* | 1/2014 | Brennenstuhl | B25F 5/026 16/426 |

* cited by examiner

*Primary Examiner* — Andrew Yang
(74) *Attorney, Agent, or Firm* — Taylor IP, P.C.

(57) ABSTRACT

An orthopedic reamer includes a drive train having a drive shaft, a reamer head connector driven by the drive shaft and a locking structure surrounding at least a portion of the drive shaft; and a handle assembly configured to detachably connect to the locking structure. The handle assembly includes a grip; a connecting structure connected to the grip that is configured to slide over the locking structure; a bridge connecting the grip to the connecting structure; a stop having a first interface feature connected to the bridge between the grip and the connecting structure; and a knob assembly at least partly surrounding the bridge having a second interface feature that is mateable to the first interface feature. The knob assembly is configured to prevent detachment of the handle assembly from the locking structure unless the second interface feature is mated with the first interface feature.

19 Claims, 7 Drawing Sheets

DETACHABLE ORTHOPAEDIC REAMER HANDLE

BACKGROUND OF THE INVENTION

1. Field of the Invention

The present invention relates to orthopaedic reamers, and, more particularly, to orthopaedic reamer handles.

2. Description of the Related Art

A hip replacement surgery is a common orthopaedic procedure that is performed when a patient's cartilage in the acetabulum joint of the hip has been damaged or destroyed, leading to bone-on-bone contact between the femoral head and the hip. The bone-on-bone contact leads to the formation of arthritic bone and cartilage, which must be removed prior to inserting the hip implant. To remove arthritic bone and cartilage, as well as create a good contact surface for installation of an acetabular cup, an acetabular reamer is used. Most acetabular reamers have a reamer head with a spherical shape and openings formed throughout the surface of the reamer head, much like a cheese grater. The reamer head is connected to a rotary driver, such as a drill, by a drive train within the reamer, and removes the diseased bone and cartilage as it spins within the acetabulum. Orthopaedic reamers are also used in other joints of the body, such as the glenohumeral joint.

Orthopaedic reamers include a handle that the user can hold on to during operation. The handle can be an integral part of the reamer or be a separable piece. Since the handle typically extends in a direction that is perpendicular to the drive train, a separable handle allows for the storage size of the orthopaedic reamer to be reduced. A separable handle can also allow for easier cleaning of the orthopaedic reamer. However, separating the handle from the rest of the orthopaedic reamer can be a time-consuming process.

What is needed in the art is an orthopaedic reamer with a handle that can quickly separate from the rest of the reamer.

SUMMARY OF THE INVENTION

The present invention provides an orthopaedic reamer that has a handle with an actuated knob assembly that has a first interface feature that can mate with a second interface feature of a locking structure of the reamer to allow for the handle to detach from the rest of the reamer.

The invention in one form is directed to an orthopaedic reamer that includes a drive train including a drive shaft, a reamer head connector driven by the drive shaft and a locking structure surrounding at least a portion of the drive shaft; and a handle assembly configured to detachably connect to the locking structure. The handle assembly includes a grip; a connecting structure connected to the grip that is configured to slide over the locking structure; a bridge connecting the grip to the connecting structure; a stop having a first interface feature connected to the bridge between the grip and the connecting structure; and a knob assembly at least partly surrounding the bridge having a second interface feature that is mateable to the first interface feature. The knob assembly is configured to prevent detachment of the handle assembly from the locking structure unless the second interface feature is mated with the first interface feature.

The invention in another form is directed to an orthopaedic reamer that includes a drive train including a drive shaft and a reamer head connector; a handle assembly configured to detachably connect to the drive train and including an actuated knob; and a locking structure surrounding at least a portion of the drive shaft and having a peripheral surface. The locking structure has a plurality of interface features on the peripheral surface that are sized to mate with the actuated knob. The handle assembly is connected to the drive train when the actuated knob is mated with at least one of the plurality of interface features.

An advantage of the present invention is that the handle can be quickly detached from the rest of the reamer without using any other tools.

Another advantage is that the handle can be easily set to different positions around the drive shaft.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
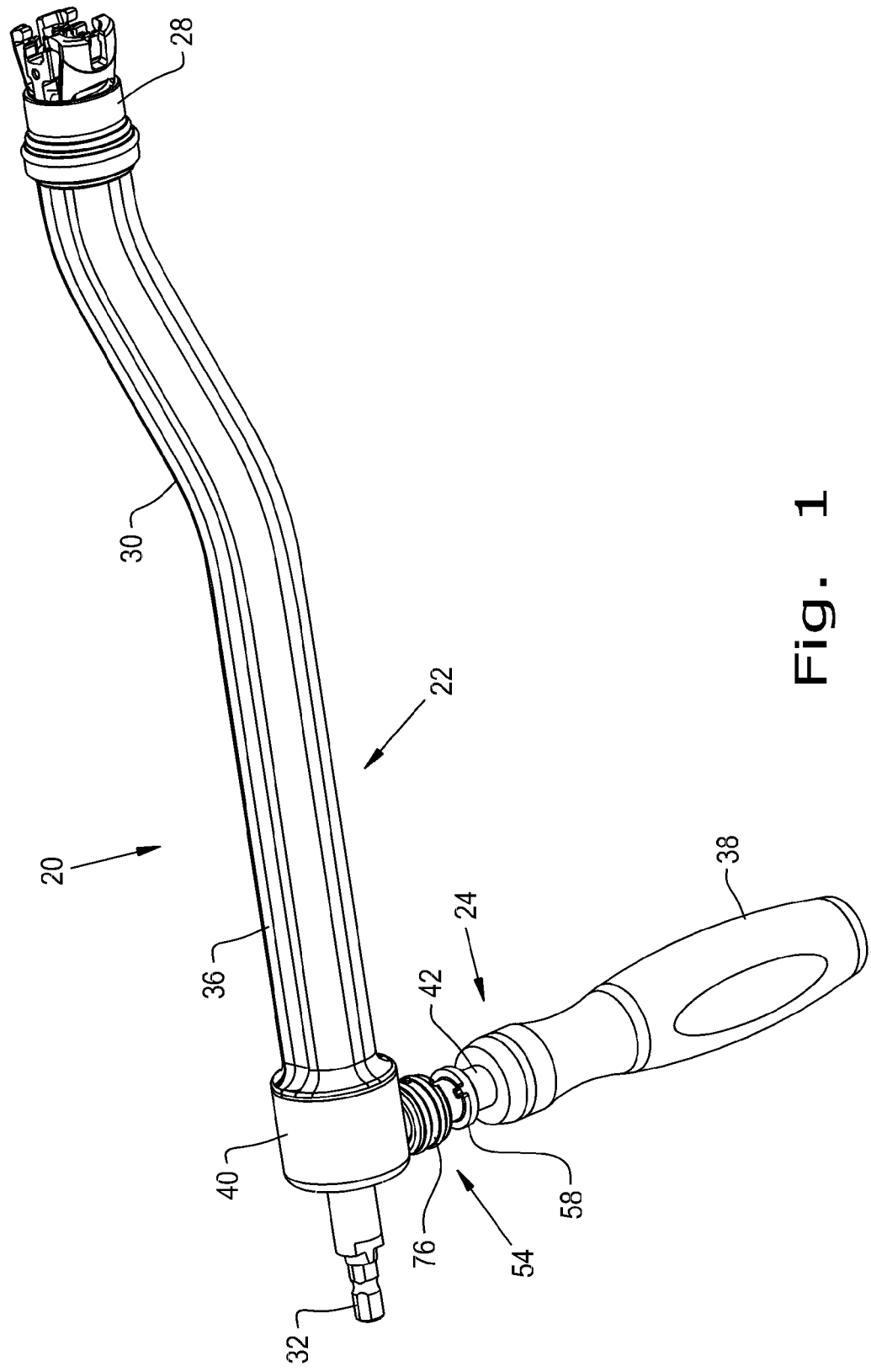
FIG. 1 is a perspective view of an embodiment of an orthopaedic reamer of the present invention.

Referring now to the drawings, and more particularly to FIG. 1, there is shown an orthopaedic reamer 20 which generally includes a drive train 22 connected to a handle assembly 24. The drive train 22 includes a drive shaft 26 (shown in FIG. 2) connected to a reamer head connector 28 that is driven by the drive shaft 26. As can be seen, the drive train 22 includes an offset 30, which allows for the reamer head connector 28 to drive a reamer head (not shown) on an axis that is parallel with a rotary driver (not shown) that is driving the drive shaft 26, but not overlapping the axis. The drive shaft 26 can be connected to the rotary driver by a shank 32 that is either an integral part of the drive shaft 26 or rotatably connected to the drive shaft 26. The drive shaft 26 transmits torque from the rotary driver to the reamer head connector 28, which will connect to the reamer head and cause the reamer head to spin, allowing for reaming to occur. The present invention contemplates that the drive shaft 26 and reamer head connector 28 can be chosen from a variety of different designs. Although the orthopaedic reamer 20 is shown in FIG. 1 as including an offset 30, the drive train 22 could also be configured as a straight drive train that does not include the offset 30. Similarly, the mechanisms used to transmit torque from the shank 32 to the reamer head connector 28 can be varied to fulfill various design criteria.

Figure 2:
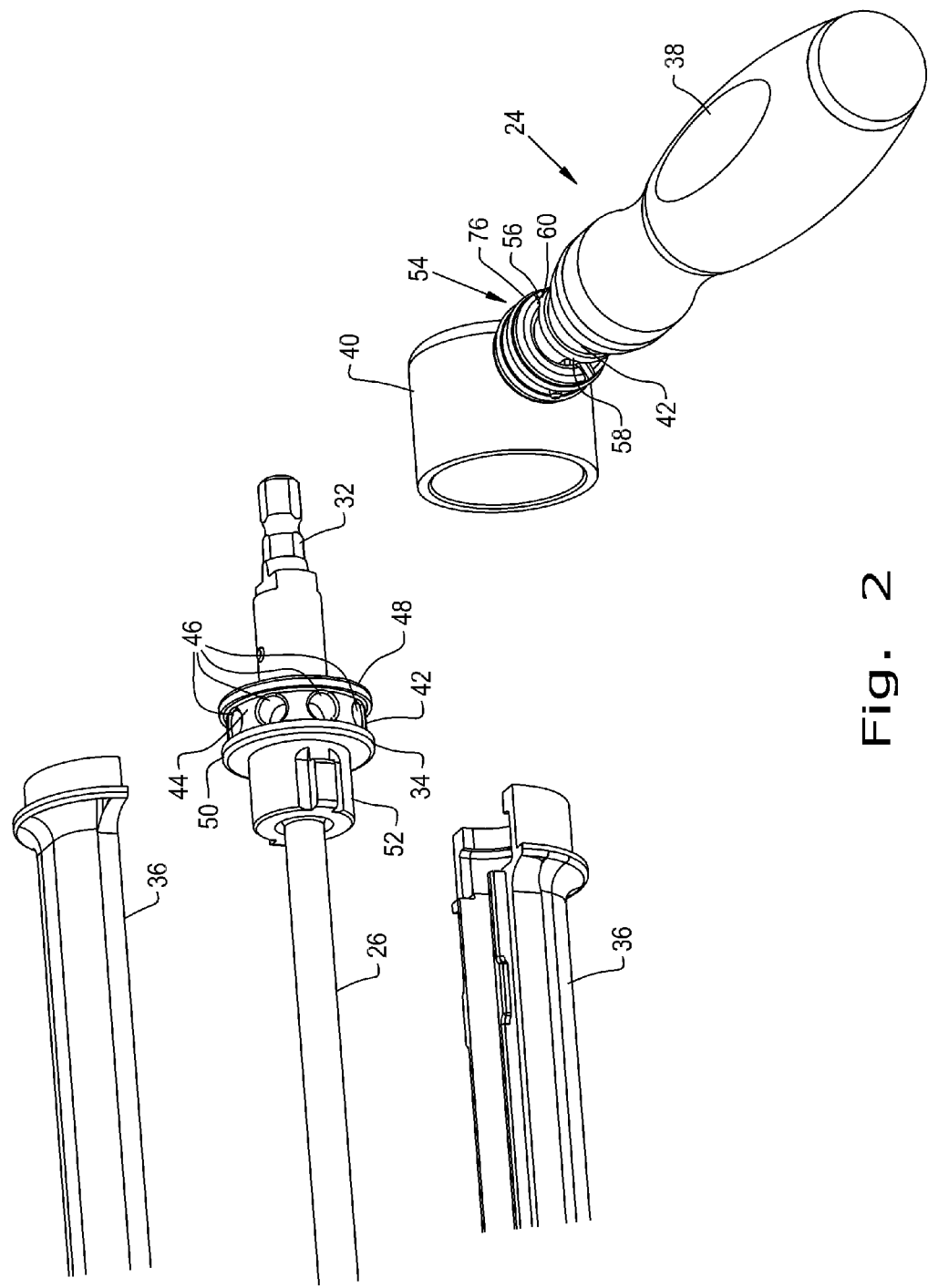
FIG. 2 is an exploded view of a section of the orthopaedic reamer shown in FIG. 1.

Referring now to FIG. 2, the handle assembly 24 and part of the drive train 22 are shown in a disassembled state. As can be seen, the drive shaft 26 is partially surrounded by a locking structure 34 adjacent to the shank 32 and a multi-part casing 36 covers the drive shaft 26 between the locking structure 34 and the reamer head connector 28. Although the locking structure 34 and casing 36 are shown as separable elements, the locking structure 34 could be incorporated as a part of the casing 36, if desired. The handle assembly 24 is shown as including a grip 38 and a connecting structure 40 that is connected to the grip 38 by a bridge 42. The grip 38 is shaped to be held during use of the orthopaedic reamer 20 during a surgical procedure. The connecting structure 40 has a shape that allows it to slide over the locking structure 34. In this respect, the shape of the connecting structure 40 can closely correlate to the shape of the locking structure 34, which is generally annular as shown, with slightly larger dimensions to allow the connecting structure 40 to surround the locking structure 34. Although the locking structure 34 and connecting structure 40 are shown as being annular, other shapes are contemplated as being used so long as the shapes do not interfere with the rotational motion of the drive shaft 26 and/or shank 32.

The locking structure 34 is shown as being generally annular, having a ring base 42 with a peripheral surface 44. Multiple mating features 46, shown as openings, are formed in the peripheral surface 44 and allow for the handle assembly 24 to be connected to the locking structure 34, which is described later. Although openings 46 are shown as the mating features 46, it is also contemplated that the mating features 46 could be configured in other ways, such as protrusions on the peripheral surface 44. The openings 46 are shown as being circular, but could be any desired shape. Ridges 48 and 50 are formed on opposing sides of the peripheral surface 44, such that the peripheral surface 44 is sandwiched in between the ridges 48 and 50, which extend farther radially than the peripheral surface 44. Ridge 50 can extend farther out than ridge 48, such that ridge 48 allows for the connecting structure 40 to slide past but ridge 50 prevents the connecting structure 40 from sliding past. This configuration can help align the handle assembly 24 with the locking structure 34 to speed up attachment and detachment of the handle assembly 24. While not shown, ridge 50 could also incorporate features that mate with the casing 36 to help keep the casing 36 components together, if the casing 36 is a separable piece. In the embodiments shown, the ridge 50 is connected to a connector 52 that mates with the pieces of the casing 36 to hold the casing 36 together.

A knob assembly 54 is placed around the bridge 42, and is shown as having a generally annular shape with gripping ridges. Although the knob assembly 54 is shown as completely surrounding a portion of the bridge 42, it is contemplated that the knob assembly 54 could only partially surround the bridge 42, if desired, to save material. As can be seen, the knob assembly 54 has an interface feature 56, shown as an indentation in the knob assembly 54. A stop 58 is also placed around the bridge 42 and has an interface feature 60 (shown in detail in FIG. 3) that is shaped to mate with the interface feature 56 formed on the knob assembly 54. As used herein, mate means that the interface features 56, 60 are complementary to each other to form a fit and/or be associated with each other. The interface features 56 and 60 can therefore be configured to have a variety of different complementary shapes. Although the stop 58 is shown as being adjacent to the grip 38 and the knob assembly 54 is shown as being adjacent to the connecting structure 40, the relative locations of the stop 58 and knob assembly 54 in this respect is contemplated as being reversed. It is also contemplated that the bridge 42, while shown as a shaft connecting the grip 38 to the connecting structure 40, could be a part of either the grip 38 or connecting structure 40. In this respect, the bridge 42 acts as a transitional area between the grip 38 and connecting structure 40 where the knob assembly 54 and stop 58 are located and does not necessarily need to be separable from the grip 38 and/or connecting structure 40.

Figure 3:
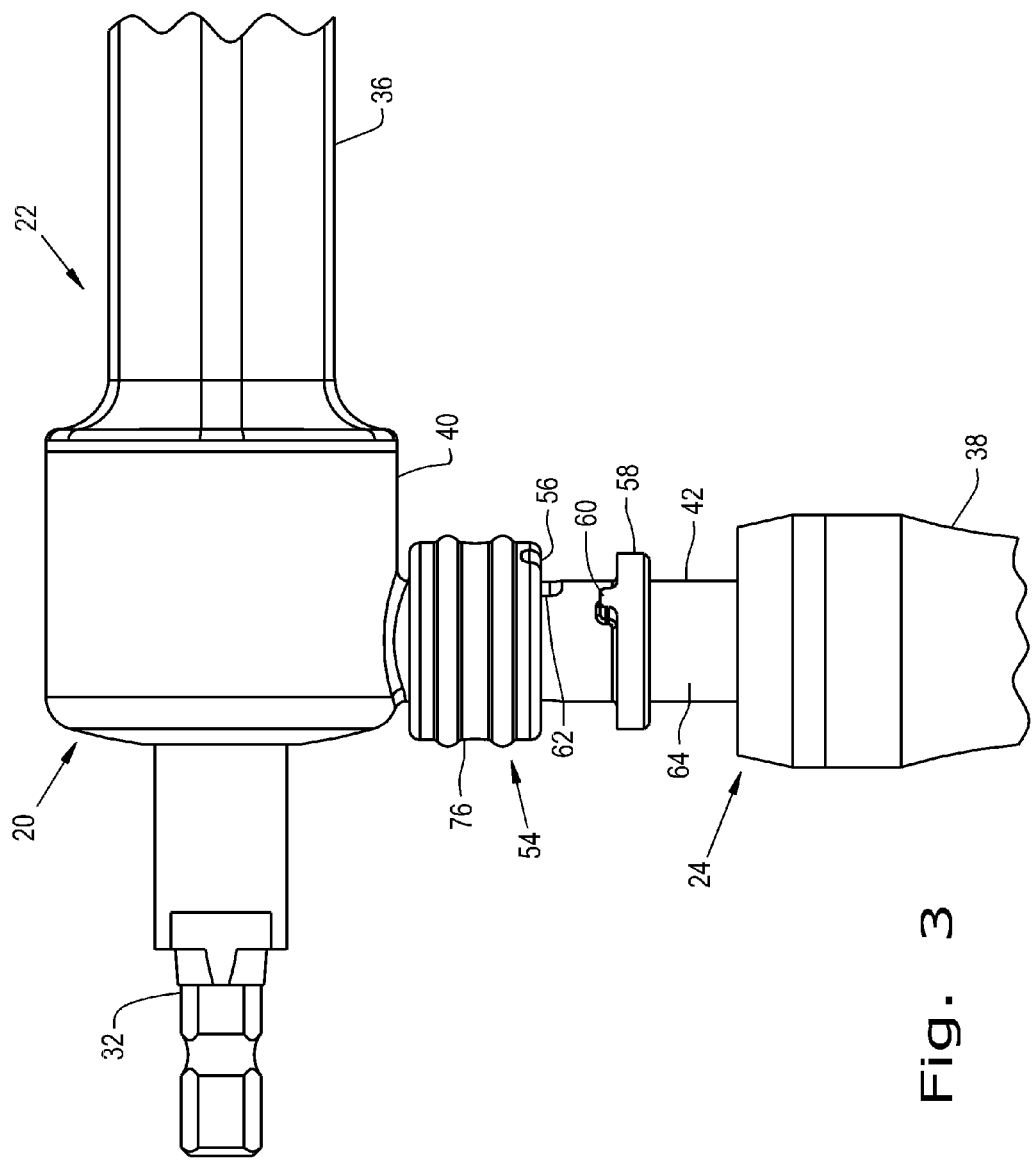
FIG. 3 is another perspective view of the orthopaedic reamer shown in FIG. 1.
Figure 4:
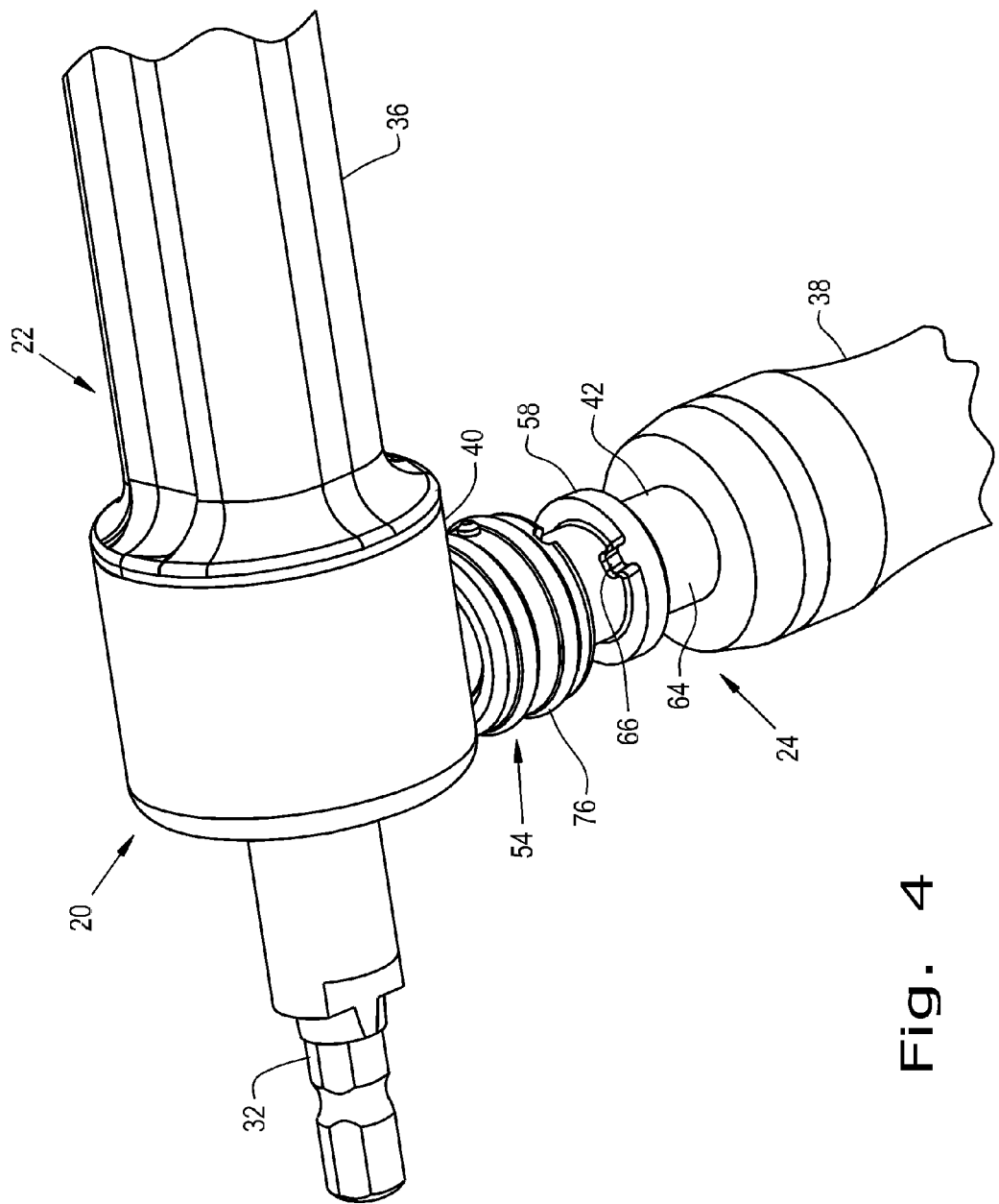
FIG. 4 is yet another perspective view of the orthopaedic reamer shown in FIG. 1.

Referring now to FIGS. 3 and 4, the handle assembly 24 is shown in better detail. As shown, the handle assembly 24 is connected to the drive train 22, with the connecting structure 40 surrounding the locking structure 34. As can be seen, the interface feature 56 of the knob assembly 54 faces the interface feature 60 of the stop 58. A slot 62 is formed in the bridge 42 and holds a part of the knob assembly 54. The slot 62 is sized so that the knob assembly 54 can be translated along the outer surface 64 of the bridge 42 and/or can be rotated about an axis of rotation defined by the bridge 42. Optionally, the slot 62 could have multiple sections, such that the knob assembly 54 would require at least some rotation to translate along the entire length of the slot 62. As shown in FIG. 3, the interface feature 56 of the knob assembly 54 is offset from the interface feature 60 of the stop 58, such that the knob assembly 54 must be rotated to align the interface features 56, 60. The reasons for this will be described later. While the interface feature 56 of the knob assembly 54 is shown as an indentation and the interface feature 60 of the stop 58 is shown as a protrusion, these configurations could be reversed such that the interface feature 56 is a protrusion and interface feature 60 is an indentation. As shown in FIG. 4, the stop 58 can also have an indentation 66 formed that mates with a protrusion (not shown) on the knob assembly 54, offering multiple interface features that mate together to give a more precise orientation of the knob assembly 54 relative to the stop 58.

Figure 5:
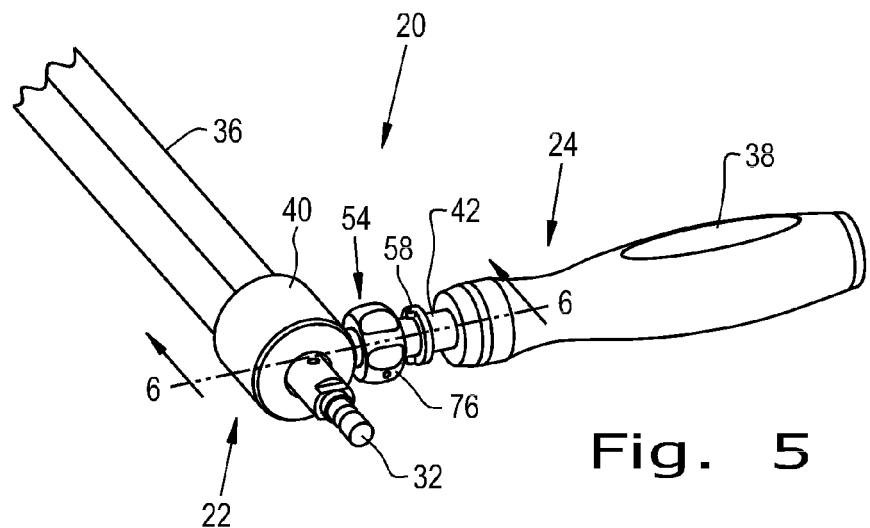
FIG. 5 is a perspective view of the orthopaedic reamer shown in FIG. 1 with the handle assembly connected to the locking structure.

Referring now to FIG. 5, a section of the orthopaedic reamer 20 is shown with the handle assembly 24 connected to the drive train 22. As can be seen, the connecting structure 40 is surrounding the locking structure 34 and the knob assembly 54 is fully advanced toward the connecting structure 40 along the bridge 42. In this position, the handle assembly 24 is firmly connected to the drive train 22 and the orthopaedic reamer 20 can be used to drive a reamer head and perform a reaming surgical procedure.

Figure 6:
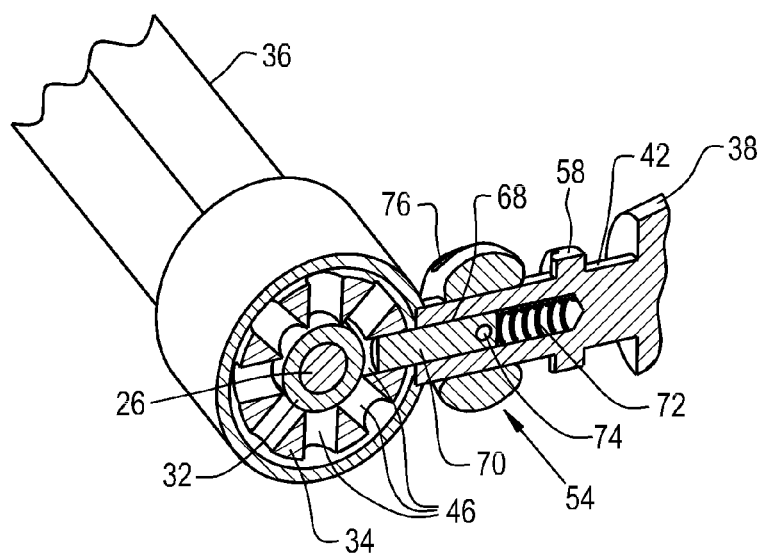
FIG. 6 is a cross-sectional view along line 6-6 of the orthopaedic reamer shown in FIG. 5.

Referring now to FIG. 6, a cross-sectional view of the orthopaedic reamer 20 in FIG. 5 is shown. As can be seen, there is a bore 68 formed within the bridge 42 that extends into the connecting structure 40. A mating feature 70, which is part of the knob assembly 54 and shown as a locking pin, is placed in the bore 68 and biased toward the connecting structure 40 by a biasing member 72, shown as a coil spring. The knob assembly 54 can further include a connector pin 74 that directly connects the locking pin 70 to a knob 76 of the knob assembly 54 such that when the knob 76 is actuated, the locking pin 70 is directly actuated as well. It is also contemplated that the locking pin 70 could be indirectly actuated by the knob 76, such that the movement of the knob 76 along the bridge 42 can produce different types of movement of the locking pin 70. When the connecting structure 40 is aligned with the locking structure 34 and the knob assembly 54 is sufficiently advanced, the locking pin 70 will rest inside one or more openings 46 and prevent sliding of the connecting structure 40 across the locking structure 34, which will keep the handle assembly 24 connected to the drive train 22. It is useful for the locking pin 70 to have a length such that it can be held within the opening 46 without advancing so far that it contacts the shank 32 and/or drive shaft 26, as this could interfere with rotational movement of the drive shaft 26. While the locking pin 70 is shown as being biased toward the connecting structure 40 by a coil spring 72, other biasing members 72 could also be used, such as a deformable material. It is also contemplated that no biasing member would be included in the bore 68, with the mating element 70 being mated with the mating feature 46 in a way that the spring 72 is not required to keep them from separating on their own.

Figure 7:
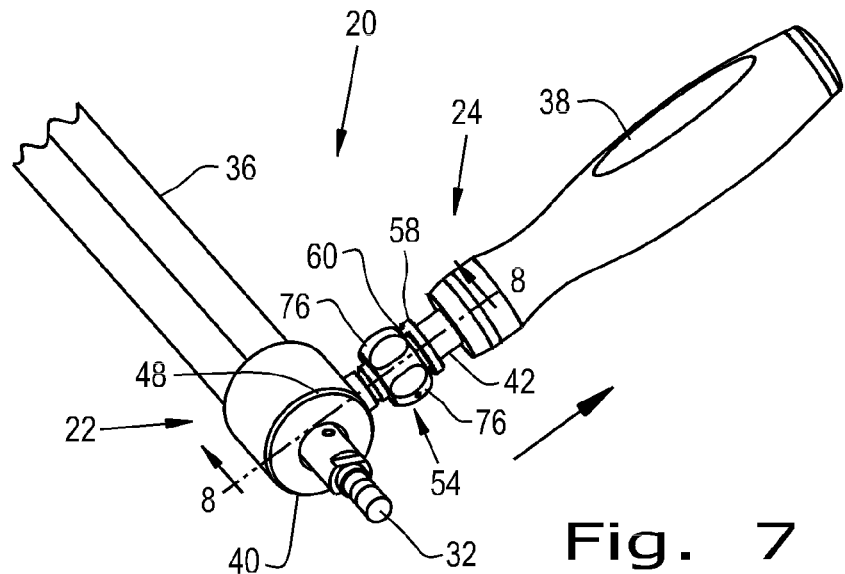
FIG. 7 is a perspective view of the orthopaedic reamer shown in FIG. 1 with the knob assembly being advanced away from the locking structure.

Referring now to FIG. 7, the orthopaedic reamer 20 is shown with the knob assembly 54 having advanced along the bridge 42 away from the connecting member 40 and toward the grip 38, as shown by the arrow. However, the knob assembly has not been fully advanced because the interface feature 60 of the stop 58 is abutting the knob 76, preventing further translation of the knob assembly 54 along the bridge 42. In this position, the handle assembly 24 is still connected to the drive train 22.

Figure 8:
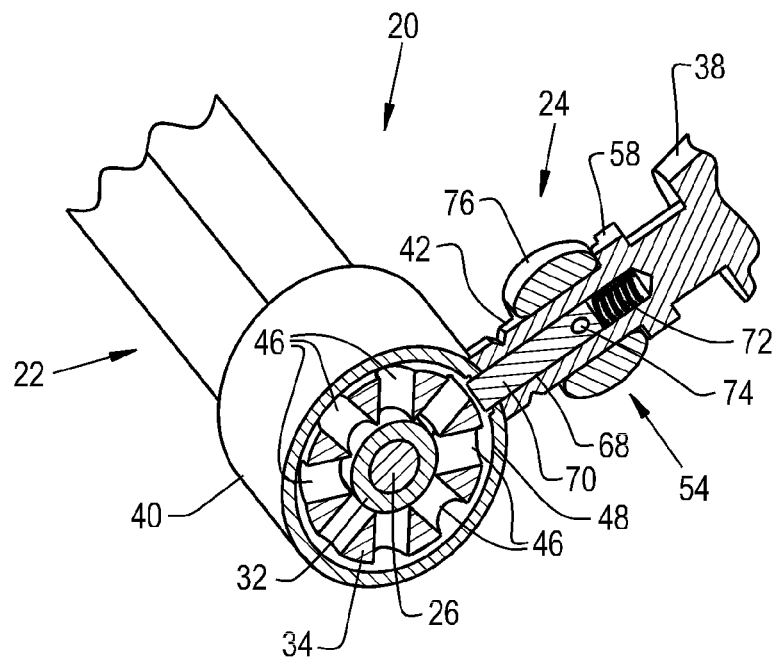
FIG. 8 is a cross-sectional view along line 8-8 of the orthopaedic reamer shown in FIG. 7.

Referring now to FIG. 8, a cross-sectional view of a portion of the orthopaedic reamer 20 in FIG. 7 is shown. As can be seen, the locking pin 70 of the knob assembly 54 has been advanced out of the opening 46 that was holding the pin 70 before. However, the locking pin 70 has not radially cleared the ridge 48, so the connecting structure 40 cannot slide off the locking structure 34. It is not necessary that the ridge 48 prevents detachment at this stage. The length of the opening 46 relative to the locking pin 70 could be adjusted such that the locking pin 70 does not advance out of the opening 46 unless the knob assembly 54 has been fully advanced.

When the orthopaedic reamer 20 is configured and positioned as shown in FIG. 8, it is possible to rotate the handle assembly 24 about the locking structure 34 so that the locking pin 70 can be held within a different opening 46. As shown, there are eight openings 46 all radially offset from each other by roughly 45 degrees, but it is contemplated that there could be any number of openings 46 with differing radial offsets. This allows for many different handle 24 positions with respect to the offset 30 to be achieved quickly. As previously described, the locking pin 70 is just an example of a possible mating element 70 that could be chosen and the openings 46 are examples of possible mating features 46 that could be chosen. It is therefore contemplated that many different configurations can be chosen that allow for the relative position of the handle 24 to be adjusted so long as the mating element 70 has not been fully actuated by the knob assembly 54, which can also be referred to as an actuated knob, and is therefore rotatably connected to the locking structure 34 without being able to detach.

Figure 9:
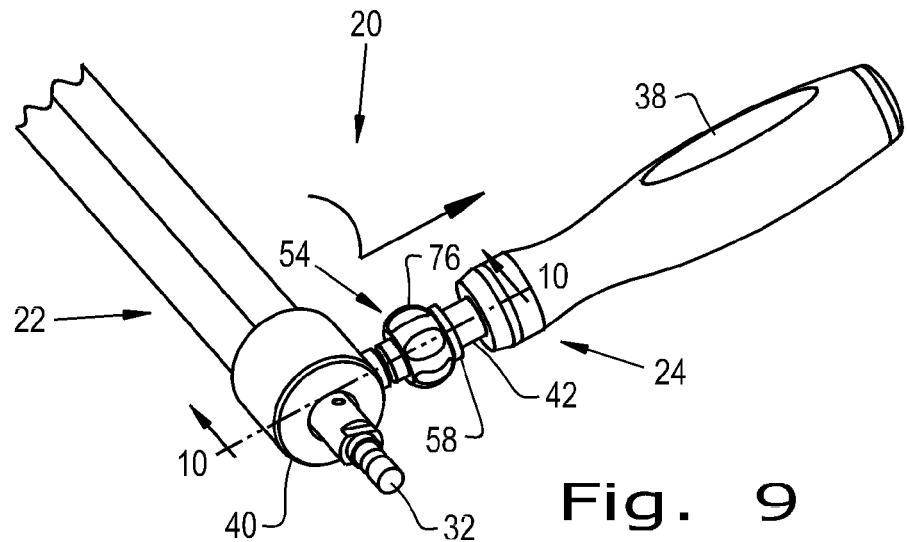
FIG. 9 is a perspective view of the orthopaedic reamer shown in FIG. 1 with the knob assembly completely advanced away from the locking structure.

Referring now to FIG. 9, the orthopaedic reamer 20 is shown with the knob assembly 54 having been rotated from its position in FIG. 7 and fully advanced, as indicated by the arrow. As previously described, the interface feature 60 of the stop 58 was abutting against the knob 76 and preventing the knob assembly 54 from being fully advanced. Since the knob assembly 54 has been rotated such that the interface feature 56 of the knob assembly 54 can mate with the interface feature 60 of the stop 58, the knob assembly 54 can be fully advanced. As shown, the interface feature 60, a protrusion, mates with interface feature 56, an indentation, by sliding into interface feature 56.

Figure 10:
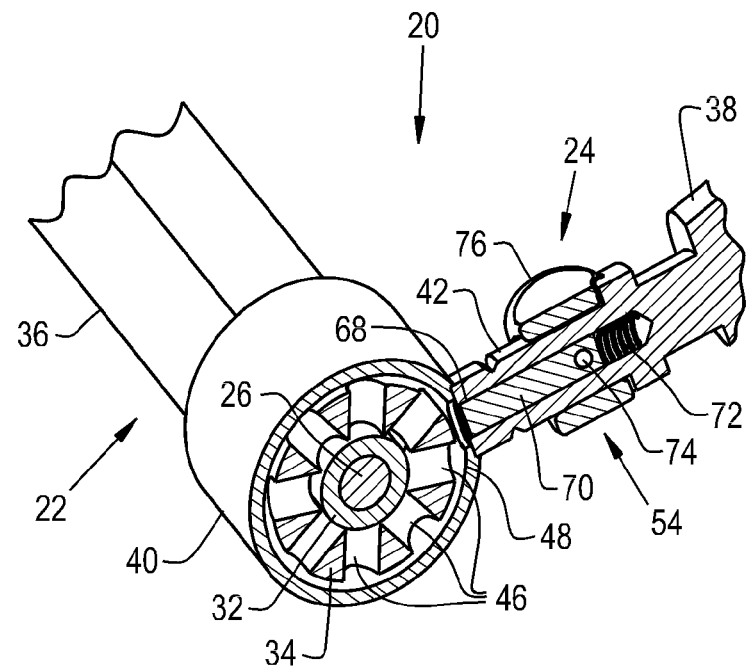
FIG. 10 is a cross-sectional view along line 10-10 of the orthopaedic reamer shown in FIG. 9.

Referring now to FIG. 10, a cross-sectional view of a portion of the orthopaedic reamer 20 in FIG. 9 is shown. As can be seen, the knob assembly 54 has been fully advanced and the locking pin 70 has radially cleared the locking structure 34. The handle assembly 24 is now free to slide off of the locking structure 34 and detach from the drive train 22.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic reamer, comprising:
   a drive train including a drive shaft, a reamer head connector driven by said drive shaft and a locking structure surrounding at least a portion of said drive shaft; and
   a handle assembly configured to detachably connect to said locking structure, said handle assembly including:
     a grip;
     a connecting structure connected to said grip that is configured to slide over said locking structure;
     a bridge connecting said grip to said connecting structure;
     a stop having a first interface feature connected to said bridge between said grip and said connecting structure; and
     a knob assembly at least partly surrounding said bridge having a second interface feature that is mateable to said first interface feature, said knob assembly configured to prevent detachment of said handle assembly from said locking structure unless said second interface feature is mated with said first interface feature.

2. The orthopaedic reamer according to claim 1, wherein said bridge includes a slot formed through that holds a portion of said knob assembly, said slot being sized to allow at least one of a rotation of said knob assembly about said bridge and a translational movement of said knob assembly along said bridge.

3. The orthopaedic reamer according to claim 2, wherein said portion of said knob assembly has one position within said slot that allows mating said first interface feature with said second interface feature.

4. The orthopaedic reamer according to claim 1, wherein said first interface feature is a protrusion and said second interface feature is an indentation that corresponds to said protrusion.

5. The orthopaedic reamer according to claim 1, wherein said second interface feature is a protrusion and said first interface feature is an indentation that corresponds to said protrusion.

6. The orthopaedic reamer according to claim 1, wherein said locking structure includes at least one opening, said bridge includes a bore that extends into said connecting structure, and said knob assembly includes a locking pin placed in said bore.

7. The orthopaedic reamer according to claim 6, wherein said locking pin is configured to prevent detachment of said handle assembly from said locking structure when it resides at least partially within said at least one opening.

8. The orthopaedic reamer according to claim 7, wherein said locking pin is directly connected to said knob assembly.

9. The orthopaedic reamer according to claim 6, further including a biasing member placed within said bore that biases said locking pin toward said connecting structure.

10. The orthopaedic reamer according to claim 6, wherein said locking structure includes a plurality of openings, said locking pin configured to prevent detachment of said handle assembly from said locking structure when it resides at least partially within at least one of said plurality of openings.

11. The orthopaedic reamer according to claim 10, wherein said plurality of openings are radially offset from one another.

12. The orthopaedic reamer according to claim 11, wherein said plurality of openings have an equal radial spacing between one another.

13. An orthopaedic reamer, comprising:
a drive train including a drive shaft and a reamer head connector;
a handle assembly configured to detachably connect to said drive train, said handle assembly including an actuated knob; and
a locking structure surrounding at least a portion of said drive shaft and having a peripheral surface, said locking structure having a plurality of mating features on said peripheral surface that are sized to mate with said actuated knob, wherein said handle assembly is connected to said drive train when said actuated knob is mated with at least one of said plurality of mating features, wherein said handle assembly includes:
a grip;
a connecting structure connected to said grip and configured to slide over said locking structure; and
a bridge connecting said grip to said connecting structure, wherein said bridge is at least partially surrounded by said actuated knob.

14. The orthopaedic reamer according to claim 13, wherein said plurality of mating features include at least one of an opening formed through said peripheral surface and a protrusion formed on said peripheral surface.

15. The orthopaedic reamer according to claim 13, wherein said locking structure has an annular shape.

16. The orthopaedic reamer according to claim 15, wherein said plurality of mating features are radially offset from one another on said peripheral surface.

17. The orthopaedic reamer according to claim 16, wherein said plurality of mating features are equally spaced apart from one another on said peripheral surface.

18. The orthopaedic reamer according claim 13, wherein said bridge includes a bore that extends into said connecting structure and said actuated knob includes a mating element disposed within said bore that mates with at least one of said plurality of mating features.

19. The orthopaedic reamer according to claim 13, wherein said bridge includes a slot formed through that holds a portion of said actuated knob, said slot being sized to allow at least one of a rotation of said actuated knob about said bridge and a translational movement of said actuated knob along said bridge.

* * * * *